United States Patent
Kujundzic et al.

(12)

(10) Patent No.: US 6,852,702 B2
(45) Date of Patent: Feb. 8, 2005

(54) 9A-N-[N'-(PHENYLSULFONYL) CARBAMOYL] DERIVATIVES OF 9-DEOXO-9-DIHYDRO-9A-AZA-9A-HOMOERYTHROMYCIN A AND OF 5-O-DESOSAMINYL-9-DEOXO-9-DIHYDRO-9A-AZA-9A-HOMOERYTHRONOLIDE A

(75) Inventors: Nedjeljko Kujundzic, Zagreb (HR); Mirjana Bukvic Krajacic, Zagreb (HR); Miljenko Dumic, Zagreb (HR); Andrea Hasenohrl, Zagreb (HR)

(73) Assignee: Pliva D.D., Zagreb (HR)

( * ) Notice: Subject to any disclaimer, the term of this patent is extended or adjusted under 35 U.S.C. 154(b) by 0 days.

(21) Appl. No.: 10/469,253

(22) PCT Filed: Feb. 27, 2002

(86) PCT No.: PCT/HR02/00010

§ 371 (c)(1),
(2), (4) Date: Aug. 28, 2003

(87) PCT Pub. No.: WO02/068438

PCT Pub. Date: Sep. 6, 2002

(65) Prior Publication Data

US 2004/0077558 A1 Apr. 22, 2004

(51) Int. Cl.$^7$ .......................... A61K 31/70; C07H 1/00; C07H 17/08
(52) U.S. Cl. .......................... 514/29; 536/7.3; 536/7.4; 536/18.5
(58) Field of Search .................. 536/7.3, 7.4, 18.5; 514/29; 534/18.5

(56) References Cited

U.S. PATENT DOCUMENTS 6,353,096 B1 * 3/2002 Leon et al. .................. 536/7.4

* cited by examiner

*Primary Examiner*—Elli Peselev
(74) *Attorney, Agent, or Firm*—Connolly Bove Lodge & Hutz, LLP

(57) ABSTRACT

9a-N-[N'-(phenylsulfonyl)carbamoyl] derivatives of 9-deoxo-9-dihydro-9a-aza-9a-homoerythromycin A and of 5-O-desosaminyl-9-deoxo-9-dihydro-9a-aza-9a-homoerythronolide A and their pharmaceutically acceptable addition salts with inorganic or organic acids are provided, along with a process for their preparation, pharmaceutical compositons, and use in treating bacterial infections.

21 Claims, No Drawings

9A-N-[N'-(PHENYLSULFONYL) CARBAMOYL] DERIVATIVES OF 9-DEOXO-9-DIHYDRO-9A-AZA-9A-HOMOERYTHROMYCIN A AND OF 5-O-DESOSAMINYL-9-DEOXO-9-DIHYDRO-9A-AZA-9A-HOMOERYTHRONOLIDE A

This application is the U.S. National Stage Under 35 U.S.C. of PCT/HR02/00010, filed Feb. 27, 2002 which in turn claims priority from Croatian Application P20010146A filed on Feb. 28, 2001.

The invention relates to 9a-N-[N'-(phenylsulfonyl) carbamoyl] derivatives of 9-deoxo-9-dihydro-9a-aza-9a-homoerythromycin A and of 5-O-desosaminyl-9-deoxo-9-dihydro-9a-aza-9a-homoerythronolide A, novel semisynthetic macrolide antibiotics from the class of azalides with antibacterial action, shown by the general formula 1

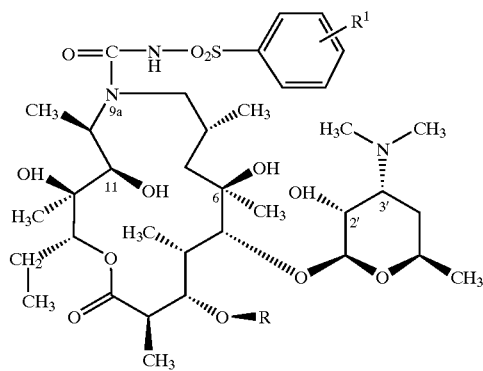

wherein R denotes H or cladinosyl radical and $R^1$ denotes H, $C_1$–$C_4$ alkyl or halogen, to their pharmaceutically acceptable addition salts with inorganic or organic acids, to a process for their preparation, to a process for the preparation of pharmaceutical compositions as well as to the use of the obtained pharmaceutical compositions in the treatment of bacterial infections.

Exythromycin A is a macrolide antibiotic, whose structure is characterized by a 14-membered macrolactone ring with a carbonyl group in C-9 position. It was discovered by McGuire in 1952 [Antibiot. Chemother., 2 (1952) 281] and has been for more than 40 years considered a safe and active antimicrobic agent in the therapy of diseases caused by gram-positive and some gram-negative microorganisms. However, in an acidic medium it is easily converted into anhydroerytfromycin A, an inactive C-6/C-12 metabolite of spiroketal structure [P. Kurath et al., Experientia 27 (1971) 362]. It is known that spirocyclisation of the aglicone ring of erythromycin A is successfully inhibited by a chemical transformation of C-9 ketone or hydroxyl groups in C-6 and/or C-12 positions. By the oximation of C-9 ketones [S. Dokić et al., Tetrahedron Lett., 1967: 1945] and subsequent modification of the obtained 9(E)-oxime into 9-[O-(2-methoxyethoxy)methyloxime]erythromycin A (ROXYIROMYCIN) [G. S. Ambrieres, FR patent 2,473, 525, 1981] or 9(S)-erythromycylamine [R. S. Egan et al., J. Org. Chem., 39 (1974) 2492] or into its more complex oxazine derivative, 9-deoxo-11-{imino[2-(2-methoxyethoxyethylidene]oxy}-9,8S)erythromycin A (DIRITHROMYCIN) [P. Lugar et al., J. Crist. Mol. Struct., 9 (1979) 329], there were synthesized novel semisynthetic macrolides, whose basic characteristics, in addition to a higher stability in an acidic medium, are better pharmacokinetics and a long biological half-life in comparison to the parent antibiotic erythromycin A. A third way for modification of C-9 ketones uses Beckmann rearrangement of 9(E)-oximes and a reduction of the obtained imino ether [G. Kobrehel et al., U.S. Pat. No. 4,328,334, 1982] into 11-aza-10-deoxo-10-dihydroerythromycin A (9-deoxo-9-dihydro-9a-aza-9a-homoerthromycin A) by enlarging the 14-membered ketolactone ring into a 15-membered azalactone ring. By a reductive N-methylation of 9a-amino group according to Eschweiler-Clark process [G. Kobrehel et al., BE patent 892,397, 1982] or preliminary protection of the amino group by conversion into corresponding N-oxides and subsequent alkylation and reduction [G. M. Bright, U.S. Pat. No. 4,474,768, 1984], there was synthesized N-methyl11-aza-10-deoxo-10-dihydroerythromycin A (9-deoxo-9-dihydro-9a-methyl-9a-aza-9a-homoerythromycin A, AZITHROMYCIN), a prototype of azalide antibiotics which are, in addition to having a wide antimicrobial spectrum including gram-negative bacteria and intracellular microorganisms, also characterized by a specific mechanism of transport to the application site, long biological half-life and short time of therapy. EP patent 0316128 (G. M. Bright) describes novel 9a-allyl- and 9a-propargyl derivatives of 9-deoxo-9-dihydro-9a-aza-9a-homoerythromycin A and U.S. Pat. No. 4,492,688 (1985, G. M. Bright) are described syntheses and antibacterial action of corresponding cyclic ethers. G. Kobrehel et al., J. Antibiot., 46 (1993) 1239–1245, further describe the synthesis and action spectrum of novel 9-deoxo-9-dihydro-9a-aza-11-deoxy-9a-homoerythromycin A 9a, 11-cyclic carbamates and their O-methyl derivatives.

By a reaction of 9-deoxo-9-dihydro-9a-aza-9a-homoerythromycin A with isocyanates or isothiocyanates respectively (N. Kujundžić, G. Kobrehel, Ž. Kelnerić, HR patent 931480, 1993), 9a-N-(N'-carbamoyl)- and 9a-N-(N'-thiocarbamoyl) derivatives of 9-deoxo-9-dihydro-9-9a-aza-9a-homoerythromycin A with a certain antibacterial activity are obtained.

It has been found—and this represents a subject of the present invention—that compounds of the general formula 1, novel semisynthetic macrolide antibiotics from the class of azalides, and their pharmaceutically acceptable addition salts with inorganic or organic acids can be prepared by a reaction of 9-deoxo-9a-aza-9a-homoerythromycin A or 5-O-desosaminyl-9-deoxo-9-dihydro-9a-aza-9a-homoerythronolide A of the general formula 2 with phenylsulfonylisocyanates and, if necessary, by a reaction of the obtained 9a-N-[N'-(phenylsulfonyl)carbamoyl derivatives of 9-deoxo-9-dihydro-9a-aza-9a-homoerythromycin A and 5-O-desosaminyl-9-deoxo-9-dihydro-9a-aza-9a-homoerythromycin A with inorganic or organic acids.

According to the lknown and established prior art, 9a-N-[N'-(phenylsulfonyl)carbamoyl derivatives of 9-deoxo-9-dihydro-9a-aza-9a-homoerythromycin A and of 5-O-desosaminyl-9-deoxo-9-dihydro-9a-aza-9a-homoerythronolide A and their pharmaceutically acceptable addition salts with inorganic or organic acids, a process for their preparation and methods of preparation and of use as pharmaceutical compositions have hitherto not been described.

It has been found that novel 9a-N-[N'-(phenylsulfonyl) carbamoyl-derivatives of 9-deoxo-9-dihydro-9a-aza-9A and of 5-O-desosaminyl-9-deoxo-9-dihydro-9a-aza-9a-homoerythronolide A of the general formula 1

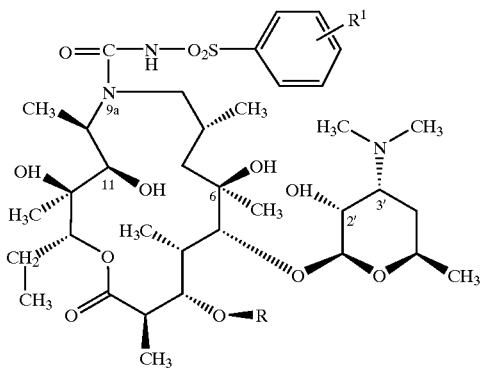

wherein R in R¹ have the above meanings, and their pharmaceutically acceptable addition salts with inorganic or organic acids may be prepared by reacting 9-deoxo-9-dihydro-9a-aza-9a-homoerythromycin A or 5-O-desosaminyl-9-deoxo-9-dihydro-9a-aza-9a-homoerythronolide A of the general formula 2, wherein R represents H or a cladinosyl radical

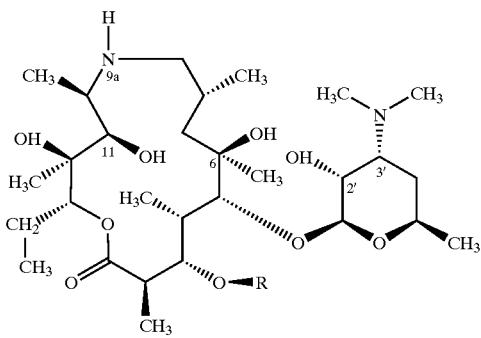

with phenylsulfonylisocyanates of general formula 3

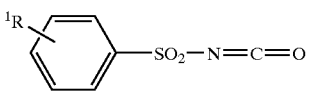

wherein R¹ has the above given meanings, in toluene, xylene or some other aprotic solvent, at a temperature from 0° C. to 110° C. in a time required for a complete conversion of the starting compound 2, preferably from 0.5 to 10 hours.

Pharmaceutically acceptable addition salts, which are also a subject of the present invention, are obtained by a reaction of 9a-N-[N'-(phenylsulfonyl)carbamoyl derivatives of 9-deoxo-9-dihydro-9a-aza-9a-homoerythromycin A and 5-O-desosaminyl-9-deoxo-9-dihydro-9a-aza-9a-homoerythonolide A of the general formula 2 with an at least equimolar amount of a corresponding inorganic or organic acid such as hydrochloric, hydroiodic, sulfuric, phosphoric, acetic, trifluoroacetic, propionic, benzoic, benzenesulfonic, methanesulfonic, laurylsulfonic, stearic, palmitic, succinic, ethylsuccinic, lactobionic, oxalic, salicylic and similar acids, in an inert solvent. The addition salts are isolated by evaporation of the solvent or, alternatively, by filtration after spontaneous precipitation or by precipitation by the addition of a non-polar co-solvent.

9a-N-[N'-(Phenylsulfonyl)carbamoyl derivatives of 9-deoxo-9-dihydro-9a-aza-9a-homoeryomycin A and of 5-O-desosaminyl-9-deoxo-9-dihydro-9a-aza-9a-homoerythronolide A of the general formula 1 and their pharmaceutically acceptable addition salts with inorganic or organic acids possess antibacterial in vitro activity. Minimal inhibitory concentrations (MIC, in $\mu$g/ml) are determined by dilution method on microplates according to recommendations of National Committee for Clinical Laboratory Standards (NCCLS, M7-A2). So e.g. the minimal inhibitory concentration on *Streptococcus pneumoniae* ATCC 6305 for the compounds from Examples 1 and 4 is 2 $\mu$g/ml and for compounds from Examples 2 and 3 is 1 $\mu$g/ml. Thus, they can be used for disinfection of rooms, surgical instruments and people as well as therapeutic agents in the treatment of infective diseases in animals, specially mammals, or humans that are caused by a wide spectrum of gram-positive bacteria, microorganisms or generally pathogenic microorganisms which are sensitive to the compounds of the formula 1. For this purpose the above compounds or their pharmaceutically acceptable salts with acids may be used orally in usual doses from 0.2 mg/kg body weight per day to about 250 mg/kg/day, most frequently from 5–50 mg/kg/day, or parenterally in the form of subcutaneous or intramuscular injections.

A process for the preparation of the compounds of the present invention is illustrated by the following examples which in no way limit the scope of the invention.

EXAMPLE 1

9-Deoxo-9-dihydro-9a-N-[N'-(4-chlorobenzenesufonyl) carbamoyl]-9a-aza-9a-homoerythromycin A 9-Deoxo-9-dihydro-9a-aza-homoerythomycin A (3.38 g, 0.0046 moles) was dissolved in toluene (40 ml) and 4-chlorobenzensulfonylisocyanate (about 1.0 g, 0.0046 moles) was added at a temperature from 0° C. to 5° C. After stirring the reaction mixture for one hour at the same temperature, the formed crystals of the crude product were sucked off. The isolation of pure 9-deoxo-9-dihydro-9a-N-[N'-(4-chlorobenzenesulfonyl)carbamoyl]-9a-aza-9a-homoerythromycin A was performed by chromatography on a silica gel column in a solvent system methylene chloride:methanol:ammonia=90:9:1.5.

IR (KBr)/cm⁻¹: 1728, 1579, 1556, 1126, 1013.

¹H NMR (500 MHz, DMSO)/δ: 4.46 (1H, H-1'), 4.91 (1H, H-1"), 3.93 (1H, H-3), 3.46 (1H, H-5), 3.34 (3H, 3"-OCH₃), 2.91 (1H, H-4"), 2.50 (6H, 3'-N'(CH₃)₂), 2.26 (1H, H-2"b), 1.52 (1H, H-2"a), 1.27 (1H, H-8), 1.23 (3H, 10-CH₃), 1.14 (3H, 3"-CH₃), 0.96 (3H, 4-CH₃), 0.82 (3H, H-5).

¹³C NMR (500 MHz, DMSO)/δ: 177.1 (C-1), 154.6 (9a-N CONH), 101.4 (C-1'), 95.8 (C-1"), 82.6 (C-5), 77.2 (C-3), 48.7 (3"-OCH₃), 44.7 (C-2), 25.7 (C-8), 20.9 (8-CH₃), 12.2 (10-CH₃), 10.7 (C-15).

MS (ES⁺) m/z (%): 952.5.

EXAMPLE 2

9-Deoxo-9-dihydro-9a-N-[N'-(p-toluenesulfonyl) carbamoyl]-9a-aza-9a-homoerythromycin A Analogously to the process described in Example 1, 9-deoxo-9-dihydro-9a-aza-homoerythromycin A (3.88 g, 0.0051 moles) was dissolved in toluene (40 ml) and p-toluenesulfonylisocyanate (1.04 g, 0.0053 moles) was added dropwise at a temperature from 0° C. to 5° C. After stirring the reaction mixture for one hour at the same temperature, the formed crystals of the crude product were sucked off. The isolation of pure 9-deoxo-9-dihydro-9a-N-[N'-(4-chlorobenzenesulfonyl)-carbamoyl]-9a-aza-9a- homoerythromycin A was performed by chromatography on a silica gel column in a solvent system methylene chloride:methanol=1:1.

IR (KBr/cm$^{-1}$): 1731, 1644, 1556, 1126, 1013.

$^1$H NMR (500 MHz, pyridine)/δ: 8.22, 8.15, 7.18 (phenyl), 5.70 (9a-NCONH), 5.40 (1H, H-13), 5.37 (1H, H-1"), 5.01 (1H, H-1'), 4.81 (1H, H-3), 4.54 (1H, H-5"), 4.11 (1H, H-5), 4.03 (1H, H-5'), 3.67 (1H, H-2'), 3.47 (1H, 3"-OCH$_3$), 3.32 (1H, H-10), 3.24 (1H, H-4"), 3.13 (1H, H-2), 2.42 (1H, 3'-N(CH$_3$)$_2$), 2.18 (3H, R-CH$_3$), 1.96 (1H, 7a), 1.91 (1H, H-8), 1.82 (1H, H-7b), 1.51 (3H, 4-CH$_3$), 1.52 (1H, 5"-CH$_3$), 0.9 (3H, H-15).

$^{13}$C NMR (500 MHz, pyridine)/δ: 179.0 (C-1), 142.7 (9a-NCONH), 130.1, 127.9, 126.9 (phenyl), 103.8 (C-1'), 95.8 (C-1"), 84.7 (C-5), 79.2 (C-4"), 79.0 (C-3), 78.0 (C-13), 75.4 (C-6), 73.7 (C-12), 72.6 (C-11), 71.4 (C-2'), 68.4 (C-5'), 66.5 (C-5"), 58.3 (C-10), 50.0 (3"-OCH$_3$), 46.5 (C-2), 43.7 (C-7), 27.8 (C-8), 19.3 (5"-CH$_3$), 15.7 (2-CH$_3$), 14.3 (12-CH$_3$), 11.8 (C-15), 10.3 (4-CH$_3$).

MS (E$^+$) m/z (%): 932.5.

EXAMPLE 3

9-Deoxo-9-dihydro-9a-N-[N'-(o-toluenesulfonyl) carbamoyl]-9a-aza-9a-homoerythromycin A Analogously to the process described in Example 1, 9-deoxo-9-dihydro-9a-aza-homoerthromycin A (3.73 g, 0.0051 moles) was dissolved in toluene (40 ml) and o-toluenesulfonylisocyanate (1.0 g, 0.0051 moles) was added dropwise at a temperature from 0° C. to 5° C. After stirring the reaction mixture for one hour at the same temperature, the formed crystals of the crude product were sucked off. The isolation of the pure 9-deoxo-9-dihydro-9a-N-[N'-(o-toluenesulfonyl)carbamoyl]-9a-aza-9a-homoerythromycin A was performed by chromatography on a silica gel column in a solvent system methylene chloride:methanol:ammonia=90:9:1.5.

IR (KBr)/cm$^{-1}$: 1727, 1633, 1556, 1126, 1013.

$^1$H NMR (500 MHz, DMSO)/δ: 7.77, 7.25, 7.14 (phenyl), 4.90 (1H, H-1'), 4.85 (1H, H-13), 4.44 (1H, H-1'), 4.01 (1H, H-5"), 3.47 (1H, H-5), 3.47 (1H, H-5), 3.69 (1H, H-5'), 3.25 (3H, 3"-OCH$_3$), 3.00 (1H, H-2'), 2.91 (1H, H-4"), 2.37 (3H, 3'-N(CH$_3$)$_2$), 2.27 (1H, H-2"a), 1.95 (1H, H-4), 1.52 (1H, H-2"b), 1.25 (1H, H-8), 1.17 (3H, 5"-CH$_3$), 1.09 (3H, 5'-CH$_3$), 0.96 (3H, 4-CH$_3$), 0.82 (3H, H-15).

$^{13}$C NMR (500 MHz, DMSO)/δ: 178.0 (C-1), 102.7 (C-1'), 95.2 (C-1"), 83.2 (C-5), 78.2 (C-4"), 78.0 (C-3), 75.8 (C-13), 74.4 (C-6), 73.7 (C-12), 73.5 (C-3"), 71.0 (C-2'), 67.7 (C-5'), 65.8 (C-5"), 65.5 (C-3'), 51.6 (3"OCH$_3$), 45.7 (C-2), 42.8 (C-4), 40.1 (3'-N(CH$_3$)$_2$), 35.4 (C-2"), 30.9 (C-4'), 25.8 (C-8), 18.3 (5"-CH$_3$), 15.6 (12-CH$_3$), 11.9 (C-15), 10.0 (4-CH$_3$).

MS (EI$^+$) m/z (%): 932.8.

EXAMPLE 4

9-Deoxo-9-dihydro-9a-N-[N'-(benzenesulfonyl) carbamoyl]-9a-aza-9a-homoerythromycin A Analogously to the process described in Example 1, 9-deoxo-9-dihydro-9a-aza-homoerythromycin A (4.01 g, 0.0055 moles) was dissolved in toluene (40 ml) and benzenesulfonylisocyanate (1.0 g, 0.0055 moles) was added dropwise at a temperature from 0° C. to 5° C. After stirring the reaction mixture for one hour at the same temperature, the formed crystals of the crude product were sucked off. The isolation of the pure 9-deoxo-9-dihydro-9a-N-[N'-(benzenesulfonyl)carbamoyl]-9a-aza-9a-homoerythromycin A was performed by chromatography on a silica gel column in a solvent system methylene chloride:methanol:ammonia=90:9:1.5.

IR (KBr)/cm$^{-1}$: 1719, 1638, 1551, 1126, 1011.

$^1$H NMR (500 MHz, DMSO)/δ: 7.84, 7.71, 7.54, 7.36 (phenyl), 4.77 (1H, H-1"), 4.44 (1H, H-1'), 4.01 (1H, H-5"), 3.21 (3H, 3"OCH$_3$), 2.90 (1H, H-4"), 2.49 (3H, 3'N(CH$_3$)$_2$), 2.26 (1H, (H-2"a), 1.76 (1H, H-14a), 1.51 (1H, H-2"b), 1.32 (1H, H-14b), 1.16 (3H, 5"-CH$_3$), 0.78 (3H, H-15).

$^{13}$C NMR (500 MHz, DMSO)/δ: 159.0, (9a-N—CO—NH), 128.8, 127.7, 126.3 (phenyl), 77.4 (C-4"), 72.7 (C-3"), 65.0 (C-5"), 49.0 (3"-OCH$_3$), 39.4 (3'-N(CH$_3$)$_2$), 35.1 (C-2"), 18.7 (5"-CH$_3$), 11.1 (C-15), 9.5 (4-CH$_3$).

MS (ES$^+$) m/z (%): 918.8.

EXAMPLE 5

9-Deoxo-9-dihydro-9a-N-[N'-(2-chlorobenzenesulfonyl) carbamoyl]-9a-aza-9a-homoerythromycin A Analogously to the process described in Example 1, 9-deoxo-9-dihydro-9a-aza-homoerythromycin A (3.38 g, 0.0046 moles) was dissolved in toluene (40 ml) and 2-chlorobenzenesulfonylisocyanate (1.0 g, 0.0046 moles) was added dropwise at a temperature from 0° C. to 5° C. After stirring the reaction mixture for one hour at the same temperature, the formed crystals of the crude product were sucked off. The isolation of the pure 9-deoxo-9-dihydro-9a-N-[N'-(2-chlorobenzenesulfonyl)-carbamoyl]-9a-aza-9a-homoerythromycin A was performed by chromatography on a silica gel column first in a solvent system methylene chloride:methanol=7:3 and then in a solvent system methylene chloride:methanol:ammonia=90:9:1.5.

IR (KBr)/cm$^{-1}$: 1728, 1579, 1126, 1012.

$^1$H NMR (500 MHz, DMSO)/δ: 7.71 (phenyl), 5.08 (1H, H-13), 4.80 (1H, H-1"), 4.49 (1H, H-1'), 4.15 (1H, H-3'), 4.03 (1H, H-5"), 3.43 (1H, H-5), 3.22 (3H, 3"-OCH$_3$), 2.91 (1H, H-4"), 2.76 (1H, H-2), 2.50 (3H, 3'-N(CH$_3$)$_2$), 2.39 (1H, H-2"a), 1.14 (3H, 3"-CH$_3$), 0.88 (3H, H-15), 0.85 (3H, 12-CH$_3$).

$^{13}$C NMR (500 MHz, DMSO)/δ: 102.0 (C-1'), 97.0 (C-1"), 85.6 (C-5), 78.5 (C-4"), 68.0 (C-3'), 65.8 (C-5"), 45.2 (C-2), 40.5 (3'-N(CH$_3$)$_2$), 49.5 (3"-OCH$_3$), 35.6 (C-2"), 21.2 (3"-CH$_3$), 18.7 (5"-CH$_3$), 14.3 (12-CH$_3$), 10.8 (C-15).

MS (EI$^+$) m/z (%): 952.9

EXAMPLE 6

9-Deoxo-9-dihydro-9a-N-[N'-(4-fuorobenzenesulfonyl) carbamoyl]-9a-aza-9a-homoerythromycin A Analogously to the process described in Example 1, 9-deoxo-9-dihydro-9a-aza-homoerythromycin A (1.46 g, 0.002 moles) was dissolved in toluene (20 ml) and a toluenic suspension of 4-fluorobenzenesulfonylisocyanate (0.4 g, 0.002 moles) was added dropwise at a temperature from 0° C. to 5° C. After stirring the reaction mixture for one hour at the same temperature, the formed crystals of the crude product were sucked off. The isolation of the pure 9-deoxo-9-dihydro-9a-N-[N'-(4-fluorobenzenesulfonyl)carbamoyl]-9a-aza-9a-homoerythromycin A was performed by chromatography on a silica gel column in a solvent system methylene chloride:methanol=7:3.

IR (KBr)/cm$^{-1}$: 1727, 1638, 1593, 1552, 1126, 1013.

$^1$H NMR (500 MHz, DMSO)/δ: 7.74, 7.71, 7.16 (phenyl, 4.78 (1H, H-1"), 4.45 (1H, H-1'), 4.01 (1H, H-5"), 3.21 (3H, 3"-OCH$_3$), 2.91 (1H, H-4"), 2.51 (3H, 3'-N(CH$_3$)$_2$), 2.27 (1H, H-2"a), 1.52 (1H, H-2"b), 1.17 (3H, 5"-CH$_3$), 1.14 (3H, 3"-CH$_3$), 0.94 (3H, H-15), 0.81 (3H, 4-CH$_3$).

$^{13}$C NMR (500 MHz, DMSO)/δ: 177.2 (C-1), 160.6 (9a-NCO), 101.1 (C-1'), 95,8 (C-1"), 84.1 (C-5), 77.2 (C-4"), 72.2 (C-3"), 64.8 (C-5"), 39.9 (3'-N(CH$_3$)$_2$), 49.1 (3"-OCH$_3$), 44.3 (C-2), 34.8 (C-2"), 29.9 (C-4'), 22.9 (5'-CH$_3$), 18.5 (5"-CH$_3$), 10.0 (C-15), 9.5 (4-CH$_3$).

MS (ES$^+$) m/z (%): 936.3.

EXAMPLE 7

5-O-Desosaminyl-9-deoxo-9-dihydro-9a-N-[N'-(p-toluenesulfonyl)carbamoyl]-9a-aza-9a-homoerythronolide A 5-O-Desosaminyl-9-deoxo-9-dihydro-9a-aza-9a-homoerythronolide A (1.0 g, 0.00173 moles) was dissolved in toluene (25 ml) and p-toluenesulfonylisocyanate (about 0.34 mg, 0.00173 moles) was added dropwise at a temperature from 0° C. to 5° C. After stirring the reaction mixture for one hour at the same temperature, the formed crystals of the crude product were sucked off. The isolation of the pure 5-O-desosaminyl-9-deoxo-9-dihydro-9a-N-[N'-(p-toluenesulfonyl)carbamoyl]-9a-aza-9a-homoerythronolide A was performed by chromatography on a silica gel column in a solvent system methylene chloride:methanol:ammonia=90:9:1.5.

IR (KBr)/cm$^{-1}$: 1726, 1171, 1129, 1075.

MS (ES$^+$) m/z (%): 774.9.

EXAMPLE 8

5-O-Desosaminyl-9-deoxo-9-dihydro-9a-N-[N'-(4-chlorobenzenesulfonyl)-carbamoyl]-9a-aza-9a-homoerythronolide A Analogously to the process described in Example 1, 5-O-desosaminyl-9-deoxo-9-dihydro-9a-aza-9a-homoerythronolide A (2.54 g, 0.0046 moles) was dissolved in toluene (50 ml) and 4-chlorobenzenesulfonylisocyanate (1.0 g, 0.00459 moles) was added dropwise at a temperature from 0° C. to 5° C. After stirring the reaction mixture for one hour at the same temperature, the formed crystals of the crude product were sucked off. The isolation of 5-O-desosaminyl-9-deoxo-9-dihydro-9a-N-[N'-(4-chlorobenzenesulfonyl)carbamoyl]-9a-aza-9a-homoerythronolide A was performed by chromatography on a silica gel column in a solvent system methylene chloride:methanol=7:3.

IR (KBr)/cm$^{-1}$: 1725, 1174, 1133, 1078.

MS (EI$^+$) m/z (%): 784.7.

EXAMPLE 9

5-O-Desosaminyl-9-deoxo-9-dihydro-9a-N-[N'-(4-fluorobenzenesulfonyl)-carbamoyl]-9a-aza-9a-homoerythronolide A Analogously to the process described in Example 1, 5-O-desosaminyl-9-deoxo-9-dihydro-9a-aza-9a-homoerythronolide A (1.0 g, 0.00173 moles) was dissolved in toluene (25 ml) and 4-fluorobenzenesulfonylisocyanate (0.36 g, 0.00173 moles) was added dropwise at a temperature from 0° C. to 5° C. After stirring the reaction mixture for one hour at the same temperature, the formed crystals of the crude product were sucked off. The isolation of the pure 5-O-desosaminyl-9-deoxo-9-dihydro-9a-N-[N'-(4-fluorobenzenesulfonyl)carbamoyl]-9a-aza-9a-homoerythronolide A was performed by chromatography on a silica gel column in a solvent system methylene chloride:methanol=7:3.

IR (KBr)/cm$^{-1}$: 1727, 1174, 1129, 1076.

MS (EI$^+$) m/z (%): 778.8.

EXAMPLE 10

5-O-Desosaminyl-9-deoxo-9-dihydro-9a-N-[N'-(benzenesulfonyl)-carbamoyl]-9a-aza-9a-homoerythronolide A Analogously to the process described in Example 1, 5-O-desosaminyl-9-deoxo-9-dihydro-9a-aza-9a-homoerythronolide A (3.055 g, 0.0055 moles) was dissolved in toluene (25 ml) and benzenesulfonylisocyanate (1.0 g, 0.0055 moles) was added dropwise at a temperature from 0° C. to 5° C. After stirring the reaction mixture for one hour at the same temperature, the formed crystals of the crude product were sucked off. The isolation of the pure 5-O-desosaminyl-9-deoxo-9-dihydro-9a-N-[N'-(benzenesulfonyl)carbamoyl]-9a-aza-9a-homoerythronolide A was performed by chromatography on a silica gel column in a solvent system methylene chloride:methanol=7:3.

IR (KBr)/cm$^{-1}$: 1728, 1176, 1128, 1077.

MS (ES$^+$) m/z (%): 760.7.

EXAMPLE 11

5-O-Desosaminyl-9-deoxo-9-dihydro-9a-N-[N'-(o-toluenesulfonyl)-carbamoyl]-9a-aza-9a-homoerythronolide A Analogously to the process described in the Example 1, 5-O-desosaminyl-9-deoxo-9-dihydro-9a-aza-9a-homoerythronolide A (2.84 g, 0.0051 moles) was dissolved in toluene (40 ml) and o-toluenesulfonylisocyanate (1.0 g, 0.0046 moles) was added dropwise at a temperature from 0° C. to 5° C. After stirring the reaction mixture for one hour at the same temperature, the formed crystals of the crude product were sucked off. The isolation of the pure 5-O-desosaminyl-9-deoxo-9-dihydro-9a-N-[N'-(o-toluenesulfonyl)carbamoyl]-9a-aza-9a-homoerythronolide A was performed by chromatography on a silica gel column in a solvent system methylene chloride:methanol=7:3.

IR (KBr)/cm$^{-1}$: 1728, 1173, 1129, 1075.

MS (EI$^+$) m/z (%): 774.7.

EXAMPLE 12

5-O-Desosaminyl-9-deoxo-9-dihydro-9a-N-[N'-(2-chlorobenzenesulfonyl)-carbamoyl]-9a-aza-9a-homoerythronolide A Analogously to the process described in Example 1, 5-O-desosaminyl-9-deoxo-9dihydro-9a-aza-9a-homoerythronolide A (2.65 g, 0.00459 moles) was dissolved in toluene (50 ml) and a toluene suspension of 2-chlorobenzenesulfonylisocyanate (1.0 g, 0.00459 moles) was added dropwise at a temperature from 0° C. to 5° C. After stirring the reaction mixture for one hour at the same temperature, the formed crystals of the crude product were sucked off. The isolation of the pure 5-O-desosaminyl-9-deoxo-9-dihydro-9a-N-[N'-(2-chlorobenzenesulfonyl)carbamoyl]-9a-aza-9a-homoerythronolide A was performed by chromatography on a silica gel column in a solvent system methylene chloride:methanol=7:3.

IR (KBr)/cm$^{-1}$: 1728, 1170, 1125, 1071.

MS (ES$^+$) m/z (%): 794.1.

What is claimed is:

1. 9a-N-[N'-(Phenylsulfonyl)carbamoyl] derivative of 9-deoxo-9-dihydro-9a-aza-9a-homoerythromycin A or of 5-O-desosaminyl-9-deoxo-9-dihydro-9a-aza-9a-homoerythronolide A of the formula 1:

wherein $R^1$ denotes H, $C_1$–$C_4$ alkyl or halogen and R denotes H or cladinosyl radical, or their pharmaceutically acceptable addition salts with inorganic or organic acids.

2. A compound according to claim 1, characterized in that $R^1$ denotes H and R denotes cladinosyl radical.

3. A compound according to claim 1, characterized in that $R^1$ denotes $CH_3$ in p-position and R denotes cladinosyl radical.

4. A compound according to claim 1, characterized in that $R^1$ denotes $CH_3$ in o-position and R denotes cladinosyl radical.

5. A compound according to claim 1, characterized in that $R^1$ denotes Cl in p-position and R denotes cladinosyl radical.

6. A compound according to claim 1, characterized in that $R^1$ denotes Cl in o-position and R denotes cladinosyl radical.

7. A compound according to claim 1, characterized in that $R^1$ denotes F in p-position and R denotes cladinosyl radical.

8. A compound according to claim 1, characterized in that $R^1$ denotes R denote H.

9. A compound according to claim 1, characterized in that $R^1$ denotes $CH_3$ in p-position an R denotes H.

10. A compound according to claim 1, characterized in that $R^1$ denotes $CH_3$ in o-position and R denotes H.

11. A compound according to claim 1, characterized in that $R^1$ denotes Cl in p-position and R denotes H.

12. A compound according to claim 1, characterized in that $R^1$ denotes Cl in o-position and R denotes H.

13. A compound according to claim 1, characterized an that $R^1$ denotes F and R denotes H.

14. A process for the preparation of 9a-N-[N'-(phenylsulfonyl)carbamoyl] derivative of 9-deoxo-9-dihydro-9-a-aza-9a-homoerythromycin A of 5-O-desosaminyl-9-deoxo-9-dihydro-9a-aza-9a-homoerythronolide A of the formula as defined in claim 1, wherein $R^1$ denotes H, $C_1$–$C_4$ alkyl or halogen and R denotes H or cladinosyl radical, characterized in that 9-deoxo-9-dihydro-9-a-aza-9a-homoerythomycin A or 5-O-desosaminyl-9deoxo-9-dihydro 9a-aza-9a-homoerythronolide A of the formula 2

Is reacted with phenylsulfonylisocyanates of formula 3 wherein $R^1$ denotes the meanings given in claim 1, in an aprotic solvent at a temperature from 0° C. to 110° C.

15. A pharmaceutical composition, characterized in that it comprises a pharmaceutically acceptable carrier and an antibacterially effective amount of a compound according to claim 1.

16. The process of claim 14 wherein the aprotic solvent comprises at least one of toluene or xylene.

17. A method for treating a patient for bacterial infection which comprises administering to a patient a compound according to claim 1 in an amount effective for treating bacterial infection.

18. A method for treating a patient for bacterial infection which comprises administering to a patient a compound according to claim 2 in an amount effective for treating bacterial infection.

19. A method for treating a patient for bacterial infection which comprises administering to a patient a compound according to claim 3 in an amount effective for treating bacterial infection.

20. A method for treating a patient for bacterial infection which comprises administering to a patient a compound according to claim 4 in an amount effective for treating bacterial infection.

21. A method for treating a patient for bacterial infection which comprises administering to a patient a compound according to claim 5 in an amount effective for treating bacterial infection.

* * * * *